United States Patent
Powell et al.

(10) Patent No.: US 11,169,975 B2
(45) Date of Patent: Nov. 9, 2021

(54) RECOGNITION QUALITY MANAGEMENT

(71) Applicant: Acxiom LLC, Conway, AR (US)

(72) Inventors: Chris Powell, Bee Branch, AR (US);
John Tindell, Perryville, AR (US);
Brandy Walsh, Springdale, AR (US);
Sarah Davis, Fayetteville, AR (US)

(73) Assignee: Acxiom LLC, Conway, AR (US)

( * ) Notice: Subject to any disclaimer, the term of this patent is extended or adjusted under 35 U.S.C. 154(b) by 464 days.

(21) Appl. No.: 16/319,651

(22) PCT Filed: Jul. 14, 2017

(86) PCT No.: PCT/US2017/042034
§ 371 (c)(1),
(2) Date: Jan. 22, 2019

(87) PCT Pub. No.: WO2018/022315
PCT Pub. Date: Feb. 1, 2018

(65) Prior Publication Data
US 2021/0279214 A1    Sep. 9, 2021

Related U.S. Application Data

(60) Provisional application No. 62/366,444, filed on Jul. 25, 2016.

(51) Int. Cl.
*G06F 16/215* (2019.01)
*G06F 11/34* (2006.01)

(52) U.S. Cl.
CPC ........ *G06F 16/215* (2019.01); *G06F 11/3409* (2013.01)

(58) Field of Classification Search
USPC ........................................................ 707/692
See application file for complete search history.

(56) References Cited

U.S. PATENT DOCUMENTS 6,112,203 A    8/2000    Bharat et al.
6,243,501 B1   6/2001    Jamali
(Continued)

OTHER PUBLICATIONS

Friedman, Ted et al., "Measuring the Business Value of Data Quality," Gartner, Inc. (2011).
(Continued)

*Primary Examiner* — Cam Linh T Nguyen

(57) ABSTRACT

A recognition quality management system and method is used to determine a final group quality grade (FGQG) for a database containing data structures pertaining to objects, where the FGQG is a single numeric score indicative of the quality of the recognition that has occurred within the database. The FGQG is calculated using a weighted algorithm incorporating at least three components: a string quality score (SQS) that is determined by a string distance calculation; an input quality score (IQS) that is determined from address confidence codes; and a link quality score (LQS) that evaluates a key field to determine grouping quality. The system and method allows for the determination of recognition quality across an entire database rather than using sampling and extrapolation, and thus leads to a higher quality result, and because the system and method is objective it allows comparison of recognition quality across competing recognition quality solutions.

29 Claims, 10 Drawing Sheets

(56) References Cited

U.S. PATENT DOCUMENTS

| | | |
|---|---|---|
| 7,162,450 B2 | 1/2007 | Ponzio, Jr. |
| 7,593,904 B1 | 9/2009 | Kirshenbaum et al. |
| 8,489,441 B1 | 7/2013 | Bivens et al. |
| 8,498,948 B2 | 7/2013 | Huang et al. |
| 8,571,333 B2 | 10/2013 | Denney et al. |
| 8,874,549 B2 | 10/2014 | Tunkelang et al. |
| 9,082,083 B2 | 7/2015 | Virkar et al. |
| 2007/0016580 A1 | 1/2007 | Mann et al. |
| 2012/0290526 A1 | 11/2012 | Gupta et al. |
| 2014/0229456 A1 | 8/2014 | Hollifield et al. |
| 2014/0304267 A1 | 10/2014 | Deng et al. |
| 2014/0317078 A1 | 10/2014 | Gallagher et al. |
| 2014/0330845 A1 | 11/2014 | Feldschuh |
| 2015/0326601 A1 | 11/2015 | Grondin et al. |
| 2016/0124946 A1 | 5/2016 | Aaron et al. |
| 2017/0006130 A1* | 1/2017 | Wouhaybi ............ G06F 11/302 |
| 2017/0091785 A1* | 3/2017 | Arangali Raghavan ..................... G06F 21/57 |
| 2017/0192967 A1* | 7/2017 | Gilder ................... G16H 10/60 |
| 2018/0004645 A1* | 1/2018 | Brown ...................... G06F 7/08 |

OTHER PUBLICATIONS

Judice, Lie Yong Koh, "Correlation-Based Methods for Biological Data Cleaning," Ph.D. Thesis, National University of Singapore (2007).

Christen, Peter, "A Survey of Indexing Techniques for Scalable Record Linkage and Deduplication," IEEE Trans. on Knowledge and Data Engineering, vol. 24, No. 9 (Sep. 2012).

Schallehn, Eike et al., "Efficient Similarity-Based Operations for Data Integration," Data & Knowledge Engineering 48, pp. 361-387 (2004).

* cited by examiner

Data Repository - Size Reductions for Combined

◩ Data Repository - Size Reductions for Combined Record Volume
▨ Data Repository - Size Reductions for Combined After Applying System and Method Business Overall Accuracy ◩ Percent Accurate   ▨ Percent Inaccurate Weekly Refresh File - Processing Time After Total Reduction After Applying System and Method (In Hours)

Monthly - Size Reduction

Record Volume    After Applying System and Method

Monthly Refresh File - Processing Time (in hours)

38.5, 7%
499.2, 93%

◪ Monthly - Processing Time Savings (in hours) Time Before
▨ Monthly - Processing Time Savings (in hours) After Applying System and Method

RECOGNITION QUALITY MANAGEMENT

TECHNICAL FIELD

The field of the invention is the determination of the quality of a recognition solution applied against a database of objects, such as a database containing data structures each pertaining to a person, household, business, or the like.

BACKGROUND ART

Data "recognition" may be defined as a process by which a collection of data structures in a database, such as records, are identified as pertaining to the same object and thus those data structures are placed into the same group. For example, given a marketing database containing hundreds of millions of records that each pertains to an individual consumer, recognition may be applied to determine that certain of these records actually pertain to the same consumer, even though the data in those records may not be identical. In a simple example, data recognition may be used to determine that a person named Jimmy Smith and a person named James R. Smith, both having the same address, are in fact the same person, even though there are two separate records in the database for this person. Other specific examples include recognizing that records pertain to the same person even though those records contain different last names (such as when a woman changes her last name after marriage), persons with different addresses but the same or similar name (such as reflected in a recent move), and persons with different "propensities" (for example, affinity for specific products or services or categories of products or services) due to a change in the person's income or interests. Recognition is not limited to consumers, and can be applied to households, businesses, or any other class of objects where a database contains multiple records or other data structures that potentially may pertain to the same object.

Continuing with the example of marketing databases, high-quality groups may include characteristics such as sufficiently similar business names and contact information; sufficiently similar address information; and other information similarity, such as telephone numbers, account numbers, and email accounts. By contrast, low-quality groups are characterized by discrepancies in this type of data, with insufficient viable information present to confirm that the records actually belong together in the same group. Characteristics of low-quality groups may include sufficiently dissimilar business names or contact information (such as completely different business names); sufficiently dissimilar address information (such as records having different suite numbers, apartment numbers, street numbers, street names, ZIP codes, or ZIP+4 codes); or insufficient or differing other information present, such as differing or missing telephone numbers, account numbers, or email accounts.

Data recognition is of great value in many industries. For example, in the case of marketing databases pertaining to consumers, data recognition provides effective customer identification to create a "single view" of the customer, thereby increasing the chances that the interaction of a retailer with that customer will result in a positive experience for that customer, and thus drive increased sales for the retailer. Using this single view, a retailer better understands its relationship with the customer, may be able to reach the customer through more marketing channels, and may more accurately identify cross-selling opportunities that will be viewed as desirable by the customer. Marketers often do not know exactly who their customers are, so they are often unable to effectively reach their intended audiences. As marketing technology improves, marketers have come to recognize that online marketing channels (email, social media, websites, etc.) and offline marketing channels (such as in-store marketing) are in fact one single marketing ecosystem; data recognition improves the marketer's ability to take advantage of these new technologies.

Accurate data recognition presents many challenges. Those challenges include, by way of example, the following: information (such as information about consumers) may be in a constant state of flux; implementing a recognition solution may be costly; business strategies for approaching data objects such as customers (i.e., business "rules") may be successively modified over time, thus requiring changes to the data recognition solution after each change; creating an initial database containing all of the necessary information to perform reasonably accurate recognition may be costly, since it may in many cases involve hundreds of millions of records or even more; and the fact that every change to the recognition solution must be thoroughly tested and audited to ensure that the changes do not in fact result in a negative impact on recognition results.

Prior art methods for creating recognition solutions, and in particular the testing and auditing of those recognition solutions, have largely been performed manually. The traditional approach involves the manual review of a sample of data, audit of this sample, and then extrapolation of the results of this sample to the database as a whole. A sample is used because manual testing and auditing is so time consuming that a review of the entire database is often impractical due to the size of the database. This approach results in incomplete insights to the effectiveness of the recognition solution as a whole, and requires many man-hours to execute successfully even though only a sample of the data is used, since effectiveness is to some extent proportional to sample size. Because of the manual elements in this approach, the results are inherently subjective, and thus different persons performing the auditing and testing may achieve different results concerning effectiveness of the recognition solution. Effectively comparing different approaches to recognition thus becomes difficult or impossible, and likewise, it is difficult or impossible to accurately compare one provider's recognition offering with that of a competitor. The time required for the manual process is a great constraint as well, because as the data is constantly changing, a manual result may take so long to generate that it no longer accurately reflects the effectiveness of the recognition solution on a database that has changed since the audit and extrapolation process began. This drives manual solutions towards smaller and smaller sample sizes, which decreases the accuracy of the recognition testing and audit due to the over-reliance on extrapolation.

What is desired then is an automated system and method for determining recognition quality that is objective, may utilize a larger portion or even the entire database of data structures for analysis rather than a small sample that is followed by extrapolation, provides a quicker turnaround for business rule changes or other changes related to the database of data structures subject to the recognition system, and an improved method to compare performance metrics for recognition solutions across products, across databases, and across competing solution offerings.

DISCLOSURE OF INVENTION

The invention is directed to a system and method that assesses overall quality on a group level for any solution using data recognition. Group quality refers to the relevance of data structures existing in groups, and also encompasses how reliable it is that two or more data structures (e.g., records) have been correctly brought together as pertaining to the same object. In certain embodiments of the present invention, the first step of an automated approach to recognition involves the analysis of the likeness of strings within a group, and potentially the reoccurrence of any other defining information within the group as well. The string analysis results in a string quality score (SQS). Other scores that are used in the recognition calculation are an input quality score (IQS) and one or more link quality scores (LQS). These scores are combined according to a formula based on the application into a final group quality grade (FGQG), which is a single numeric value (such as but not limited to a value between 1 and 100, with 100 being the highest quality), which is assigned to each group to reflect the quality of the recognition that data structures in this group do in fact pertain to the same object. In this way, a numeric value is used as a scoring mechanism directly related to overall group quality. The score may be interpreted as a percentage; for example, if a FGQG of 95 is found, this may be described as a 95% result, indicative of high quality and highly reliable data. A threshold cutoff value may be applied in order to suppress groups that are deemed to be of low quality (i.e., a numeric value below the threshold cutoff value, thus indicating a low confidence in the accuracy of the grouping).

The invention reduces storage requirements for a production database because grouped data that are deemed unacceptable (i.e., below the cut-off threshold value) are suppressed, and the resulting production environment will consist of only the high-scoring groups. Because the number of groups is reduced, it follows that processing times for any applications using this data are reduced in the production environment since fewer groups needs to be processed.

The invention provides users with a real-time snapshot of the objects to which the data structures pertain, such as retail customers, thereby eliminating lag time and improving the ability of the user to make informed business decisions in a timely manner. This is of particular importance in certain applications, such as the serving of online marketing messages in response to a user accessing a particular website or social media outlet, which must be performed in real time so that the user's experience is not degraded as a result of the service. Recognition quality measurement using the older manual method would be impossible in a real-time, online environment.

The invention provides an objective measure of recognition quality, thereby allowing for the objective analysis of the results of changing certain aspects of the database (e.g., business rules) to determine the effect that such changes have on recognition quality. Likewise, the numerical measure may be used to objectively compare competing recognition offerings so that a customer may make an informed decision concerning alternative recognition solutions.

Although simply automating the prior art manual techniques could potentially improve sample size, it may be seen that such an approach would not allow for the objective analysis as described above and the advantages that flow therefrom. The present invention represents a complete departure from the subjective approach used in previous manual methods of analyzing recognition quality.

These and other features, objects and advantages of the present invention will become better understood from a consideration of the following detailed description of the preferred embodiments and appended claims in conjunction with the drawings as described following:

BRIEF DESCRIPTION OF DRAWINGS

FIG. 1-B is an overview of the consumer record reductions observed when implementing one embodiment of this system and method on the data repository of a data service company providing a recognition solution.

FIG. 1-C is an overview of the record reductions observed when implementing one embodiment of this system and method on the data repository of a data service company providing a recognition solution.

FIG. 2-B is an overview of the accuracy audit of the FGQG according to an embodiment of the invention by score range.

FIG. 3-B is an overview of total processing time and the reductions observed when implementing an embodiment of the invention on the weekly refresh process.

FIG. 3-C is an overview of monthly size reduction observed when implementing an embodiment of the invention.

FIG. 3-D is an overview of monthly refresh file processing time and the reductions observed when implementing an embodiment of the invention.

FIG. 4-B is a schematic showing the FGQG logic as incorporated into the data recognition solution shown in FIG. 4-A.

FIG. 5-B is an overview of the reductions in hard disc storage requirements for processing observed when implementing an embodiment of the invention on a identity resolution data repository.

FIG. 5-C is an overview of the reductions in hard disc storage requirements for processing observed when implementing an embodiment of the invention on a identity resolution data repository.

BEST MODE FOR CARRYING OUT THE INVENTION

Figure 1A:
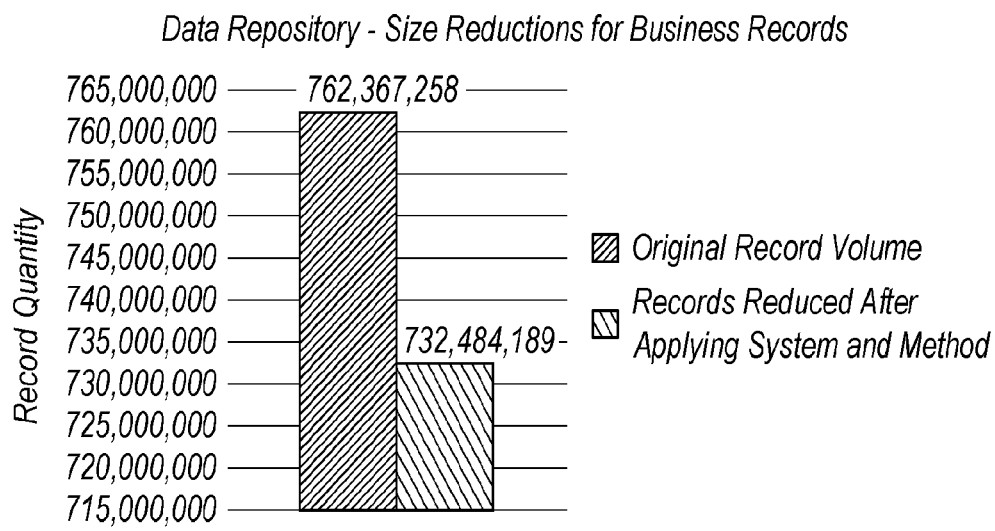
FIG. 1-A is an overview of the business record reductions observed when implementing one embodiment of this system and method on the data repository of a data service company providing a recognition solution.
Figure 1B:
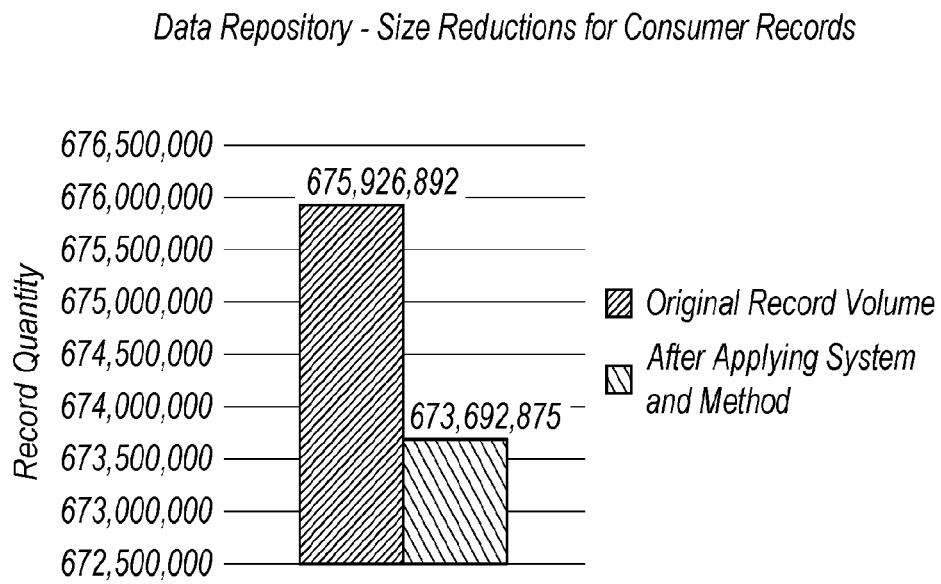
Figure 1C:
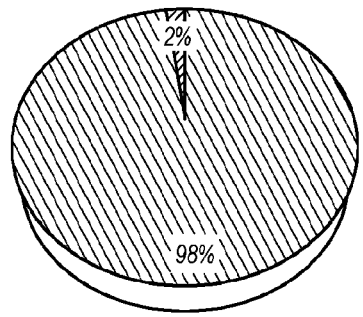
Figure 2A:
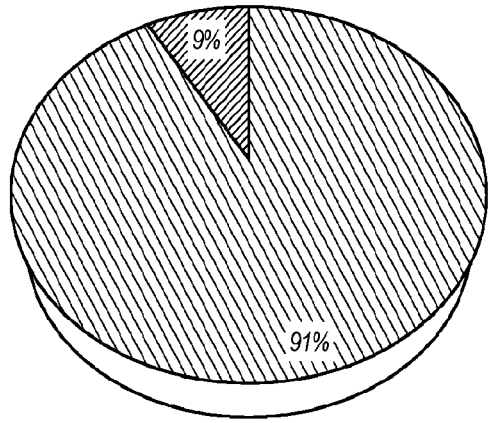
FIG. 2-A is an overview of the accuracy audit of the final group quality grade (FGQG) according to an embodiment of the invention.
Figure 2B:
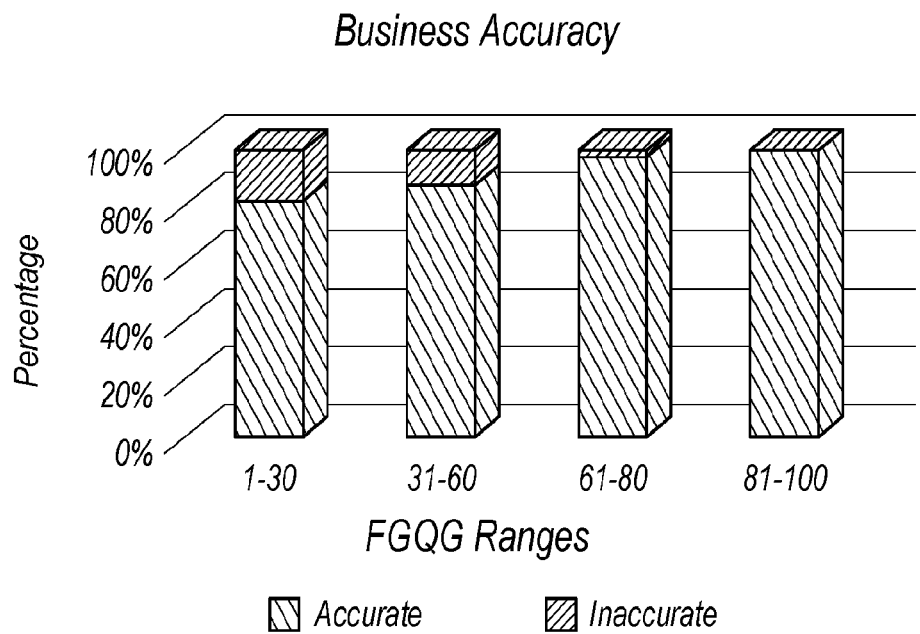
Figure 3A:
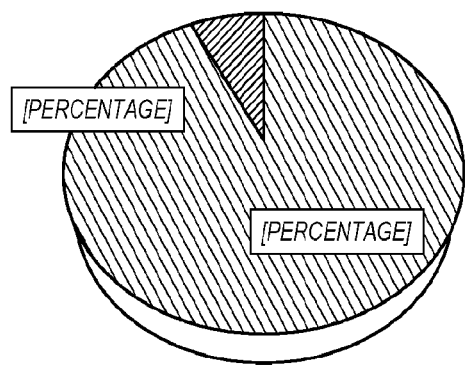
FIG. 3-A is an overview of the number of records processed and the reductions observed when implementing a weekly refresh process according to an embodiment of the invention.
Figure 3B:
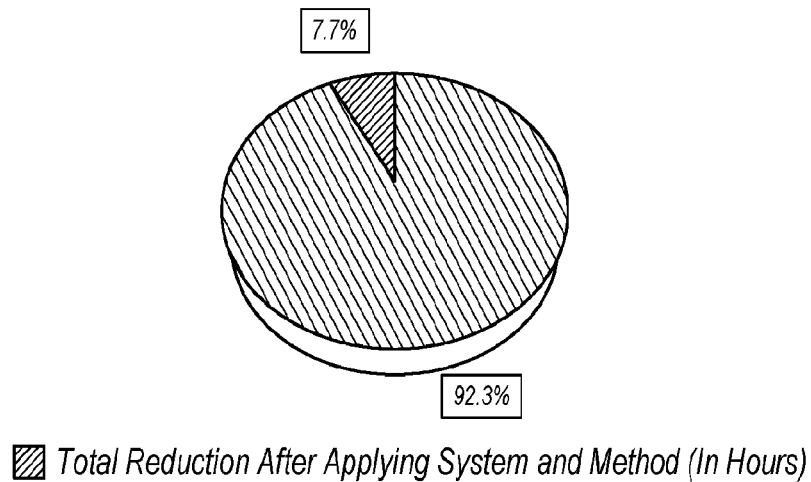
Figure 3C:
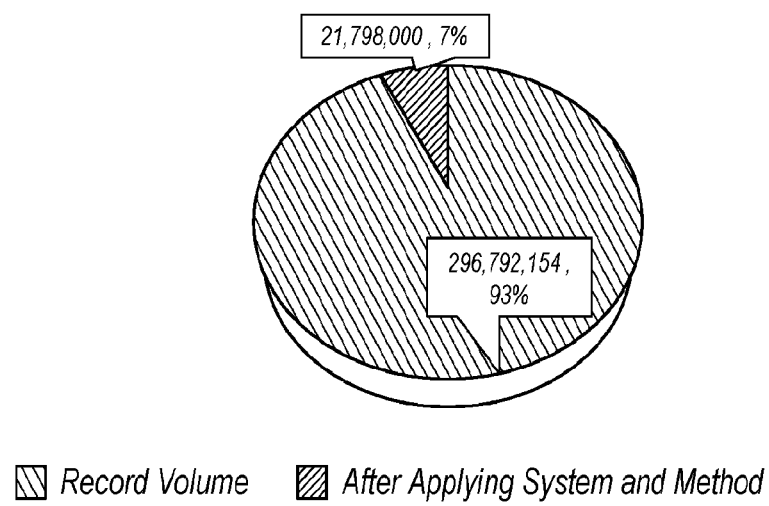
Figure 3D:
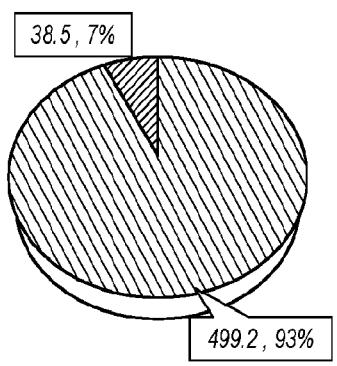

Before the present invention is described in further detail, it should be understood that the invention is not limited to the particular embodiments and implementations described, and that the terms used in describing the particular embodiments and implementations are for the purpose of describing those particular embodiments and implementations only, and are not intended to be limiting, since the scope of the present invention will be limited only by the claims.

The following definitions are used in describing the embodiments set forth below:

Business record: a row containing identifying elements unique to a single business. e.g., business name, business address, business phone, etc.

Consumer record: a row containing identifying elements unique to an individual consumer. e.g., consumer name, consumer address, consumer phone, etc.

Business group: a cluster of business records pertaining to a single business; high-quality groups contain records with sufficiently similar characteristics.

Consumer group: a cluster of consumer records pertaining to a single consumer; high-quality groups contain records with sufficiently similar characteristics.

Confidence code: a custom rule set designed to aid users in creating auto-decisioning rules and used in the evaluation of match results.

Quality Indicator: values produced by a postal processing product to indicate the overall deliverability of the address.

Link Field: generally refers to CLQS, AOLQS, and/or BLQS (as each are defined below).

Over-chained Group: a low-quality group that contains clusters of records likely pertaining to multiple consumers or businesses.

Account numbers: Client or third-party account numbers associated with business and/or consumer records, one account number pertains to one individual.

Maintained Link (M): a string of characters indicating that a data provider's identity resolution tools have previously identified or ingested a specific record.

Derived Link (M): a string of characters indicating that a specific record is new, and has not yet been identified or ingested by the data provider's identity resolution tools.

Group size categories may be employed in an effort to more accurately analyze the entire repository of data structures and prevent biased results. The following group size categories shown in Table 1 were applied in an embodiment of the invention as will be described following.

TABLE 1

| Group Size Category | Record Count Range |
|---|---|
| Tiny | 2-3 records |
| X-Small | 4-8 records |
| Small | 9-20 records |
| Medium | 21-50 records |
| Large - A | 51-100 records |
| Large - B | 101-250 records |
| Large - C | 251-500 records |
| X-Large A | 501-1,000 records |
| X-Large B | 1,001-3,000 records |
| X-Large C | 3001-10,000 records |
| XX-Large A | 10,001-20,000 records |
| XX-Large B | 20,001-50,000 records |
| XX-Large C | 50,001+ records |

In an effort to account for both business and consumer records in an embodiment that is directed to data objects related to marketing, two methodologies have been developed for assessing the overall group quality of these two types of objects. All records in the described embodiments will follow the methodology outlined, although the invention is not so limited. The weighting of each scoring component is correlated with the size category of the group. The weightings of the scoring components are broken down into three sections below, according to the size category of the group. Note that CBLQS is the consumer business link quality score, AOLQS is the address only link quality score, and CLQS is the consumer link quality score, all of which values are described in greater detail below.

a. Tiny, X-Small, and Small:
  i. FGQG (Business Groups)=SQS(0.10)+IQS(0.40)+ CBLQS(0.30)+AOLQS(0.20)
  ii. FGQG (Consumer Groups)=SQS(0.10)+IQS(0.40)+ CLQS(0.30)+AOLQS(0.20)
b. Medium
  i. FGQG (Business Groups)=SQS(0.10)+IQS(0.25)+ CBLQS(0.40)+AOLQS(0.25)
  ii. FGQG (Consumer Groups)=SQS(0.10)+IQS(0.40)+ CLQS(0.30)+AOLQS(0.20)
c. Large (A, B, C), X-Large (A, B, C), and XX-Large (A, B, C)
  i. FGQG (Business Groups)=SQS(0.10)+IQS(0.00)+ CBLQS(0.65)+AOLQS(0.25)
  ii. FGQG (Consumer Groups)=SQS(0.10)+IQS(0.40)+ CLQS(0.30)+AOLQS(0.20)

1. String Quality Score—SQS

This SQS is a score with a value in the range of 1-100 formed by analyzing the likeness of the strings present in the concatenated fields. For example, (COMPANY_NAME, STREET_NUMBER, PRE_DIRECTIONAL, STREET_SUFFIX, POST_DIRECTIONAL, SECONDARY_UNIT_DESIGNATOR, SECONDARY_NUMBER) and MAX & MIN are found for each group with Oracle MIN/MAX functions in an Oracle database environment. It analyzes the physical input of the data.

2. Input Quality Score—IQS

The IQS analyzes the following five fields of confidence codes (CDs) and indicators (INDs) shown in Table 2:

TABLE 2

| Field | Score Range |
|---|---|
| OVERALL_QLTY_IND | 1-6 |
| ADDRESS_QLTY_IND | 1-9, X |
| NDIV_CONF_CD | 1-6, 0 |
| ADDR_CONF_CD | 1-5 |
| BUS_CONF_CD | 1-6, 0 |

The confidence codes and indicators of Table 2 have a 3-step equation. The max score for each code is implemented into the following equation:

$$\text{Confidence or Quality Indicator Calculation} = 100 * \left( \frac{(\text{Max} + 1) - (\text{Actual Score})}{\text{Max}} \right)$$

Each score's ratio is dependent on the max score. All the scores from the confidence and indicators are added together then multiplied by the confidence code overall weight. All five confidence codes and quality indicators are weighted equally at 20%. Each indicator has a maximum value. Values such as X and 0 (zero) are replaced with (Max+1) so that it receives a grade of 0% for its portion of the IQS.

3. Link Quality Score—LQS

The link quality score (LQS) is a general component of the interim group quality grade (GQG) that determines the quality of different link fields. It can be applied to any link field. In the preferred embodiment this shows up in the group quality gauge (GQG) formula as Business Link Score (BLQS), Address Only Link Score (AOLQS), Consumer Link Score (CLQS), and so on. The expressions represented below are simplified versions (more detailed versions are shown further below) of the original expression. The main LQS formulas are as follows:

$$LQS = \left(\frac{100*M*T*\left(R-U+\left(1.5-\left(\frac{U}{R}\right)\right)\right)}{R^2}\right)$$

$$CLQS = \left(\frac{100*M*T*\left(R-U+\left(1.5-\left(\frac{U}{R}\right)\right)\right)}{R^2}\right)$$

$$BLQS = \left(\frac{100*M*T*\left(R-U+\left(1.5-\left(\frac{U}{R}\right)\right)\right)}{R^2}\right)$$

$$CBLQS = BLQS + \left(\left(1-\frac{BLQS}{100}\right)*CLQS\right)$$

where U is the number of unique links within a link field for the group; R is the number of records within the group; U(max) or M is the count of the unique link that occurs most often, and T is the T equation.

The CBLQS is a variation of LQS that first calculates the BLQS and then adjusts the score based on a percentage of remaining points and the CLQS in order to account for the value of the consumer links within business groups. This is used to properly grade groups that contain both business and consumer records. It is only used when calculating a GQG on business groups.

To calculate M, if the string that is M contains "00MSUS0" then the following equation is used:

$$M = \left(\left(1-\frac{M}{R}\right)*M+M\right)$$

This equation works like an exception and occurs at the end. For example, a group having R=4, U=3, M=2 will get an LQS score of 0. (If the equation is applied to this example group, M becomes 3 and the group gets an actual LQS score, rather than 0; this is not the intended result).

If the string that is M contains "00MSUS1," then M=count of the link group that occurs most often. This portion of the M calculation logic is to be ignored if the MDP Exception (Exception 5 below) is met.

In order to graph the T Equation, the y-axis is the T Constant, and the x-axis is the ratio of unique values to records, i.e., U/R. Specifically, the following values are applied to T:
 i. If Group Size='TINY','XSMALL' & (U/R)≤0.364:
    T=−0.5(U/R)+1
 ii. If Group Size='TINY','XSMALL' & (U/R)>0.364:
    T=−1.2(U/R)+1.2
 iii. If Group Size !='TINY','XSMALL': T=−0.5(U/R)+1
4. Exceptions
The following five exceptions apply to the LQS Formula (5 Total):
Exception 1: This exception keeps the LQS of groups with an M of 1 at a zero. This exception reduces processing time. The logic applied is that M must be ≥2. If M Is<2, then LQS=0. Please note that the M referenced in the above comparison is the instance of M after the maintained calculation has taken place.
Exception 2: This exception bypasses the rest of the LQS calculation and gives a group with exact link matches a 100 for the LQS. This reduces processing time as well. The logic applied is that if M=R, then LQS=100.
Exception 3: This exception allows null values to be counted for the U in the calculation for business groups. It affects only Business Groups. The logic applied is that if Record_Type='B' & Business_Link Is Null, then count the null value for U but not for M.
Exception 4: This exception allows null values to be counted for the U in calculation for consumer groups. It affects only Consumer Groups. The logic applied is that if Record_Type='C' & Consumer Link Is Null, then count the null value for U but not for M.
Exception 5 (M Decrease Percentage or MDP): This exception allows for a comparison of the two most-occurring unique links in order to better discern over-chained groups. When calculating M we need to create a loop in order to find the first two Ms (M1 and M2) corresponding to the two most-occurring unique links. The total number of records (R) also needs to be derived for this calculation. This calculation and loop will happen before the maintained M calculation. The values will be used to create two ratios to compare in order to determine if the group is truly over-chained and the M value needs to be decreased. The M that comes out of this will be the value that is used to calculate the adjusted M if the M string contained '00MSUS0'. If the string did not contain '00MSUS0' then the M maintained calculation is skipped and the result of this calculation is assigned to M. This logic supersedes the logic outlined above with respect to a string that is M and contains '00MSUS0.' The affected groups sizes are those that are X-Large A and larger. All group types are affected. Variables are M1 (the value derived from the first loop through the group to find the non-null M that occurs most often); M2 (the value derived from the second loop through the group to find the next most frequently occurring non-null M value); and R (the total number of records in a group). The formulas applied are:

$$MDP=M2/M1$$

$$MDPCV=M1/R$$

MDPCV is a ratio of the link that occurs most often in a group to the total number of records in the group, according to the equation:

Let MDPT=(M1+M2)/R

If MDPT>=0.9 and string that occurs most often contains '00MSUS0':
  M=M1
  Run M Calculation
Else If MDPT>=0.9 and string that occurs most often contains '00MSUS1'
  M=M1
Else If MDPT<0.9
  If MDP>MDPCV and string that occurs most often contains '00MSUS0':
    M=M1(1−MDP)
    Run M Calculation
  Else If MDP>MDPCV and string that occurs most often contains '00MSUS1':
    M=M1(1−MDP)
  Else If MDP<=MDPCV and string that occurs most often contains '00MSUS0':
    M=M1
    Run M Calculation
  Else If MDP<=MDPCV and string that occurs most often contains '00MSUS1':
    M=M1

The described implementation of the invention also includes a number of other exceptions that impact the overall FGQG. The account numbers exception exists to allow the analysis of the account numbers in a group. It affects all group sizes and business and consumer groups. The equation (set forth below) will be applied to each group after the initial GQG is calculated. Null fields are included in this calculation. Any and all nulls will count as one "unique" for the purposes of this exception. For any other purpose null fields will have no value. Nulls or blanks will not be considered as the account number UMAX (ANU). For example, if no account numbers are present in a 10 record group ANU=0, UAN=1, R=10. Of the exception calculations, these are to be calculated first. Here, ANU is M in the group for the account number field; UAN is the total number of unique account numbers; and R is the total number of records in the group. The applicable equation is:

$$FGQG = \left(\left(\frac{100-GQG}{3}\right)\left(\frac{ANU}{R}\right)\left(1-\frac{UAN-1}{R}\right)\right) + GQG$$

The business match exception exists to ensure that groups that have exact matches on certain fields get a 100 for their link score. It affects all group sizes, but business group types only. It is to be calculated after the account calculation and will only be calculated if the following field values are exact matches: COMPANY_NAME, SUBURB, STATE, and POSTCODE. The following equations are applied only if there is an exact match for all of the four fields previously listed:

BLQB=SQS

The consumer exact match exception ensures that small groups that have exact matches on certain fields get a 100 for their link score. This only applies to Consumer Tiny or Extra Small groups that have an AOLQS and/or CLQS score of 50 or less. The logic applied is that if STREET_NUMBER, STREET_NAME, SUBURB, STATE, POSTCODE are equal throughout the group, then

AOLQS=SQS

The first name/last name exception is implemented in order to solve issues where the score is being significantly reduced by a flip flop of the first and last names within a record. It applies to all group sizes but only to groups of the consumer type. The logic applies is as follows:

```
String = FIRSTNAME + LASTNAME of first record
String 1 = FIRSTNAME + LASTNAME
String 2 = LASTNAME + FIRSTNAME
    If String 1 == String
        Then Match Count ++;
    Else if
        String 2 == String
    Then Match Count ++;
    Else if
        Do nothing
    If matchRate >= .5 && CLQS < 50
    then CLQS = match Rate*100;
```

The key indicator calculation (KIC) exception compares the phone numbers within a group. Nulls are not counted in this exception. To utilize the logic for this exception, P must be greater than 0 and C must be greater than or equal to 2. It affects all group sizes and all group types. The applicable formulas are:

$$FGQG = FGQG + \left(\left(\frac{100-FGQG}{\left(2-\frac{FGQG}{100}\right)}\right)(KIC)\right)$$

$$KIC = AO,$$

$$O = \frac{P}{R}$$

Where A=agreement, O=occurrence, P=phone numbers present, C=count of the unique phone number that occurs most often, R=number of records within the group; and U=number of unique phone numbers in the field. The logic applied is:
If P>0 AND C>=2
Then $$FGQG = FGQG + \left(\left(\frac{100-FGQG}{\left(2-\frac{FGOG}{100}\right)}\right)(KIC)\right)$$

Else:
FGQG=FGQG

The secondary numbers exception compares the secondary numbers (field id=Secondary_Number) within the group. Nulls are not counted in this exception. To utilize the logic for this exception, P must be greater than 0 and P/R must be greater than or equal to a defined constant based on group size. The variables listed are different from the variables utilized in the KIC Exception logic. This is to be calculated after every other exception. It affects all group sizes and all group types. The applicable formulas are:

$$FGQG = FGQG - \left(FGQG * \left(\frac{1-\frac{C}{P}}{1.3}\right)\right)$$

$$P/R$$

$$C/P$$

Where P=secondary numbers present (excluding nulls), C=the count of the unique secondary number that occurs most often (excluding nulls); and R=the count of the records within the group. The logic applied is:

1. If $P > 0$ AND SIZE_BAND == 'TINY' AND $P/R >= .79$

Then $$FGQG = FGQG - \left(FGQG * \left(\frac{1-\frac{C}{P}}{1.3}\right)\right)$$

2. Else If $P > 0$ AND SIZE_BAND == 'XSMALL' AND $P/R >= .79$

Then $$FGQG = FGQG - \left(FGQG * \left(\frac{1-\frac{C}{P}}{1.3}\right)\right)$$

3. Else If $P > 0$ AND SIZE_BAND == 'SMALL' AND $P/R >= .79$

Then $$FGQG = FGQG - \left(FGQG * \left(\frac{1-\frac{C}{P}}{1.3}\right)\right)$$

-continued

4. Else If $P > 0$ AND SIZE_BAND == 'MEDIUM' AND $P/R >= .77$ Then $$FGQG = \left(FGQG * \left(\frac{1-\frac{C}{P}}{1.3}\right)\right)$$

5. Else If $P > 0$ AND SIZE_BAND == 'LARGE_A' AND $P/R >= .59$ Then $$FGQG = FGQG - \left(FGQG * \left(\frac{1-\frac{C}{P}}{1.3}\right)\right)$$

6. Else If $P > 0$ AND SIZE_BAND == 'LARGE_B' AND $P/R >= .59$ Then $$FGQG = FGQG - \left(FGQG * \left(\frac{1-\frac{C}{P}}{1.3}\right)\right)$$

7. Else If $P > 0$ AND SIZE_BAND == 'LARGE_C' AND $P/R >= .53$ Then $$FGQG = FGQG - \left(FGQG * \left(\frac{1-\frac{C}{P}}{1.3}\right)\right)$$

8. Else If $P > 0$ AND SIZE_BAND == 'XLARGE_A' AND $P/R >= .53$ Then $$FGQG = FGQG - \left(FGQG * \left(\frac{1-\frac{C}{P}}{1.3}\right)\right)$$

9. Else If $P > 0$ AND SIZE_BAND == 'XLARGE_B' AND $P/R >= .50$ Then $$FGQG = FGQG - \left(FGQG * \left(\frac{1-\frac{C}{P}}{1.3}\right)\right)$$

10. Else If $P > 0$ AND SIZE_BAND == 'XLARGE_C' AND $P/R >= .50$ Then $$FGQG = \left(FGQG * \left(\frac{1-\frac{C}{P}}{1.3}\right)\right)$$

11. Else If $P > 0$ AND SIZE_BAND == 'XXLARGE_A' AND $P/R >= .47$ Then $$FGQG = FGQG - \left(FGQG * \left(\frac{1-\frac{C}{P}}{1.3}\right)\right)$$

12. Else If $P > 0$ AND SIZE_BAND == 'XXLARGE_B' AND $P/R >= .46$ Then $$FGQG = FGQG - \left(FGQG * \left(\frac{1-\frac{C}{P}}{1.3}\right)\right)$$

13. Else If $P > 0$ AND SIZE_BAND == 'XXLARGE_C' AND $P/R >= .42$ Then $$FGQG = FGQG - \left(FGQG * \left(\frac{1-\frac{C}{P}}{1.3}\right)\right)$$

14. Else $$FGQG = FGQG$$

The LQS formula having been previously introduced, the following is a more detailed explanation of the original LQS formula.

$$LQS, AOLQS, CLQS, BLQS = \left(1 - \left(\frac{\left(U - \left(1.5 - \frac{U}{R}\right)\right)}{R}\right)\right)\left(\left(\frac{M}{R}\right)(T)\right)*100$$

1. Variables
   a. R
      i. Simply a count of the records within a group
   b. U
      i. Count of unique links within a group
   c. M
      i. Calculated by taking a count of the two most frequently occurring links within a group, comparing formulas, and entering logic based off of the formula comparisons.
      ii. The count of the link that occurs most often is defined as the variable M1. The link that has the second largest count is defined as the variable M2.
      iii. The formulas are as follows: MDP=M2/M1, MDPCV=M1/R, MDPT=(M1+M2)/R
      iv. Links can either be maintained or derived. Maintained links are more valuable than derived links
      v. To account for this additional logic was implemented:

If MDPT>=0.9 && M1 is Maintained:
M=M1

$$M = \left(\left(1 - \frac{M}{R}\right) * M + M\right)$$

Else If MDPT>=0.9 && M1 is Derived:
M=M1
Else If MDPT<0.9
If MDP>MDPCV && M1 is Maintained:
M=M1(1−MDP)

$$M = \left(\left(1 - \frac{M}{R}\right) * M + M\right)$$

Else If MDP>MDPCV && M1 is Derived:
  M=M1(1−MDP)
Else If MDP<=MDPCV && M1 is Maintained:
  M=M1

$$M = \left(\left(1 - \frac{M}{R}\right) * M + M\right)$$

Else If MDP<=MDPCV M1 is Derived:
  M=M1
  vi.

$$M = \left(\left(1 - \frac{M}{R}\right) * M + M\right)$$

The above formula simply adds back a percentage of M back to itself in order to properly account for the fact that a maintained link is more valuable than a derived link.

2. Components:
   a. When the count of the link that occurs most often (M) is equal to Records (R), LQS is equal to 100. When M is being calculated null link fields are completely ignored. Groups that meet these criteria do not utilize this expression.
      i. The logic behind this is: When M occurs as often as R in a group there is a 100% match on the links thus the group needs to receive a 100 for the LQS score. This also cuts down on processing time.
   b. This portion $$\left(1 - \left(\frac{\left(U - \left(1.5 - \frac{U}{R}\right)\right)}{R}\right)\right)$$

is a relationship between the number of unique links and the number of records.
      i. The logic behind this portion of the expression is this: As the U to R ratio within a group increases the score will decrease and the opposite is true as well; as the U to R ratio decreases the score will increase. The number of unique links is being decreased by a relationship of Unique Links (U) to Records (R). For example, 3 Uniques (U) in a group with an R of 5 will get a lower score than a group with a U of 3 and an R of 100.
      ii. The constant 1.5 was chosen based on an optimized graphical representation of the expression.
      iii. Groups where the count of the link that occurs most often (M) is less than 2 do not utilize this expression.
   c. This portion $$\left(\left(\frac{M}{R}\right)(T)\right)$$

is a relationship between M and R.
      i. This relationship is then multiplied by the corresponding T Constant (T). T is calculated by a linear relationship between U and R. The precise linear relationship is selected based on group size (more detail below).
      ii. The logic behind this portion of the expression is this: As the M to R ratio within a group increases the score will increase and the opposite is true as well; as the M to R ratio decreases the score will decrease.
   d. This portion*100 converts the decimal to a whole number.
   e. The AOLQS, BLQS, and the CLQS follow the same formula and logic. We chose to follow the same logic because all of the link fields behave the same (save for the fact that they display link information for a different set of fields), for ease of use and to avoid confusion.
   f. T Equations
      i. The T equation accelerates or decelerates the U to R relationship based on group size (R). It adds in a third dimension to alter the ratios in order to advance or inhibit the rate at which the score decreases based on group size (R).
      ii. The logic behind this is: As the group sizes change, the accuracy of the U to R and M to R ratios becomes less indicative of the group quality. The T adds a third factor to address the concerns around the previously mentioned observation and to increase the accuracy of the ratios within the group.
         (1) For example, a group with a U to R ratio of 10 to 200 or 10 to 2000 can be of similar or lower quality as a group with a U of 10 and an R of 20 even though the larger groups have lower U to R ratios. This is due to the fact that there could be 10 groups of 20 or 10 groups of 200.
      iii. The T Equations were chosen with consideration of their linear representations in order to modify the M to T relationship based on the relationship of U to R and on R separately. The logic behind this is that the greater the count of Unique Links, the greater the 'link disagreement' within the group. On the graph of a T Equation, the y-axis is the T Constant, and the x-axis is the ratio of uniques to records, i.e. U/R
      iv. If Group Size=='Tiny' or 'XSmall' AND $$\left(\frac{U}{R}\right) \leq 0.364$$

use:

$$T = -0.5\left(\frac{U}{R}\right) + 1$$

(1) We chose these restrictions to ensure that the equation would be truly indicative of the group quality.

(2) −0.5 is present in order to make it more indicative of the group's U to R ratio.
(3) +1 is present in order to keep the equation in the correct graphical bounds.
(4) We chose to restrict the group ranges to Tiny and XSmall because this equation only holds true within groups of these sizes.
(5) We chose (U/R)≤0.364 to ensure that the equation would be truly indicative of the group quality.

v. If Group Size=='Tiny' or 'XSmall' AND $$\left(\frac{U}{R}\right) > 0.364$$

use:

$$T = -1.2\left(\frac{U}{R}\right) + 1.2$$

(1) −1.2 is present in order to decrease the score at a more rapid rate.
(2) +1.2 is present to set the minimum value so that the outcome will always be positive.
(3) We chose to restrict the group ranges to Tiny and XSmall because this equation is only truly indicative within groups of these sizes.
(4) We chose (U/R)>0.364 to ensure that the equation would be truly indicative of the group quality.

vi. If Group Size!='Tiny' or 'XSmall' use:

$$T = -0.5\left(\frac{U}{R}\right) + 1$$

(1) −0.5 is present in order to make it more indicative of the group's U to R ratio.
(2) +1 is present in order to keep the equation in the correct graphical bounds.
(3) * CLQS It is then multiplied against the CLQS to take a percentage of the CLQS score. We chose to multiply the modified BLQS against the CLQS to take into account the consumer records in the group.
(4) BLQS+ That number is added back to the BQLS. We chose to add the modified score back to the BLQS to have an accurate portrayal of the business to consumer records in the group. We chose to add to BLQS rather than CLQS because the formula will only be applied to the business groups, thus we want BLQS and business records to have a heavier weight in the link score. This also allows the CLQS to make up for some short comings or discrepancies in the business link score.

The following is a breakdown of the simplification of the original LQS formula in order for one to understand the simplified version listed previously.

$$LQS = \left(1 - \left(\frac{\left(U - \left(1.5 - \frac{U}{R}\right)\right)}{R}\right)\right)\left(\left(\frac{M}{R}\right)(T)\right) * 100$$

-continued $$= \left(\frac{M*T*100}{R}\right) - \left(\frac{\left(U - \left(1.5_R - \frac{U}{R}\right)\right)}{R}\right) * \left(\frac{M*T*100}{R}\right)$$

$$= \left(\frac{M*T*100}{R}\right) - \left(\frac{U*M*T*100 - \left(1.5 - \frac{U}{R}\right)*M*T*100}{R^2}\right)$$

$$= \left(\frac{R}{R}\right)\left(\frac{M*T*100}{R}\right) - \left(\frac{U*M*T*100 - \left(1.5 - \frac{U}{R}\right)*M*T*100}{R^2}\right)$$

$$= \left(\frac{R*M*T*100}{R^2}\right) - \left(\frac{U*M*T*100 - \left(1.5 - \frac{U}{R}\right)*M*T*100}{R^2}\right)$$

$$= \left(\frac{R*M*T*100 - U*M*T*100 + \left(1.5 - \frac{U}{R}\right)*M*T*100}{R^2}\right)$$

$$= \left(\frac{100*M*T*\left(R - U + \left(1.5 - \frac{U}{R}\right)\right)}{R^2}\right)$$

Figures 1, 4A:
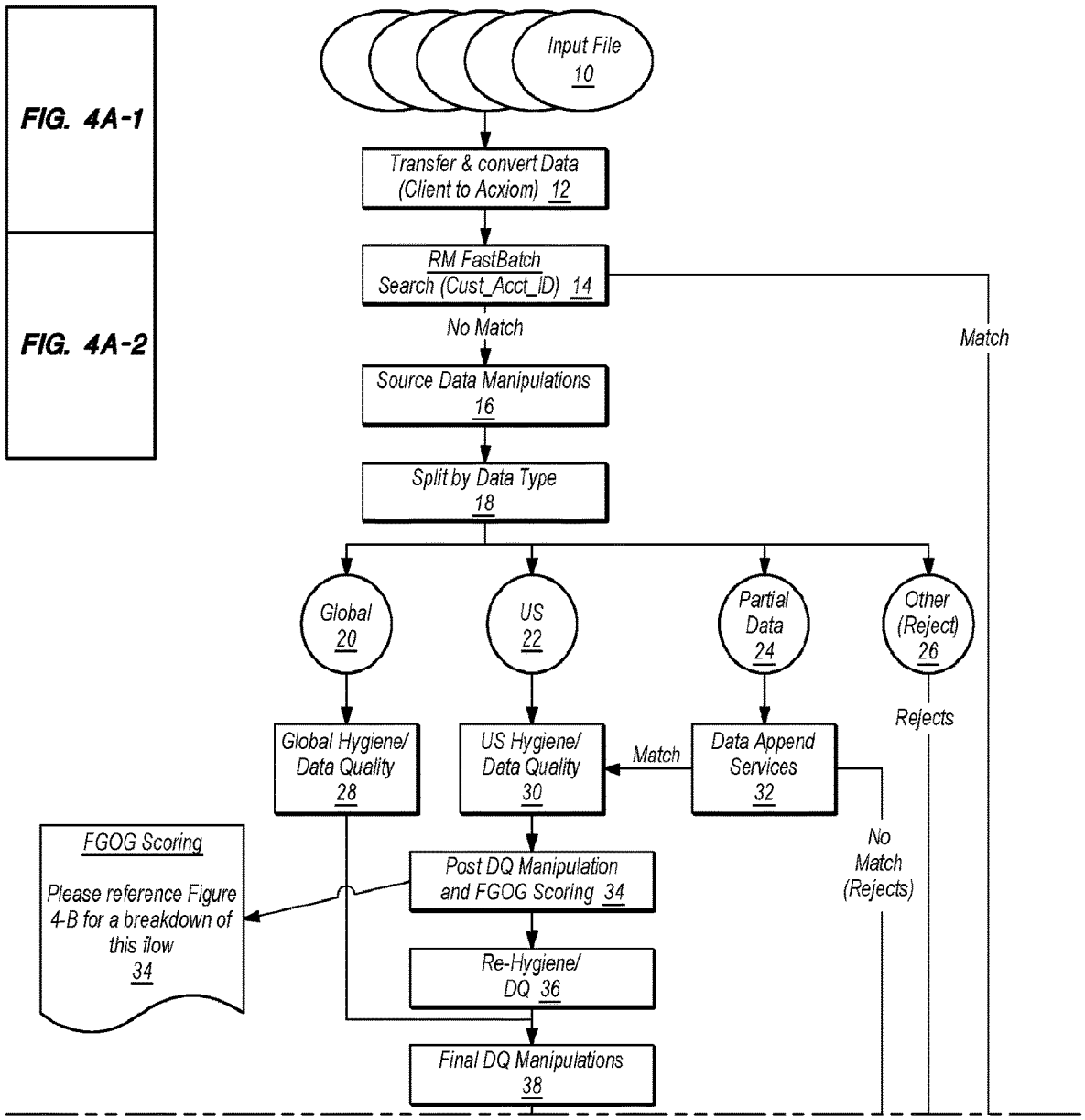

Referring now to FIGS. 1-A to 3-D, the results of test runs applying the embodiment of the invention described above may be illustrated. The data used for the first test consisted of 792,250,327 business records and 678,160,909 consumer records. The cut-off threshold for this test was a FGQG score of 40, which means that for each group receiving an FGQG of less than 40, that group was suppressed in the final result. Using the embodiment described herein on this test data, the number of records identified as a business was reduced by 3.77% (or 29,883,069 records), and the number of records identified as consumers was reduced by 0.33% (or 2,234,017 records). These results are graphically illustrated in FIGS. 1-A to 1-C. It will be understood that by reducing the number of records in the applicable database by millions, significant process improvements are recognized in the recognition technology platform. The reduced number of records reduces storage requirements, while it also reduces processing time. The latter is a result of the fact that each business process applied to the database requires an iteration for each record, and thus the reduction in record count results in a reduction in processing time for each business process. Since a single database may be used for a great many business processes in any given time period such as a week or month, the reduction in overall processing time for the marketing provider or its data services provider can be very significant.

Figures 2, 4A:
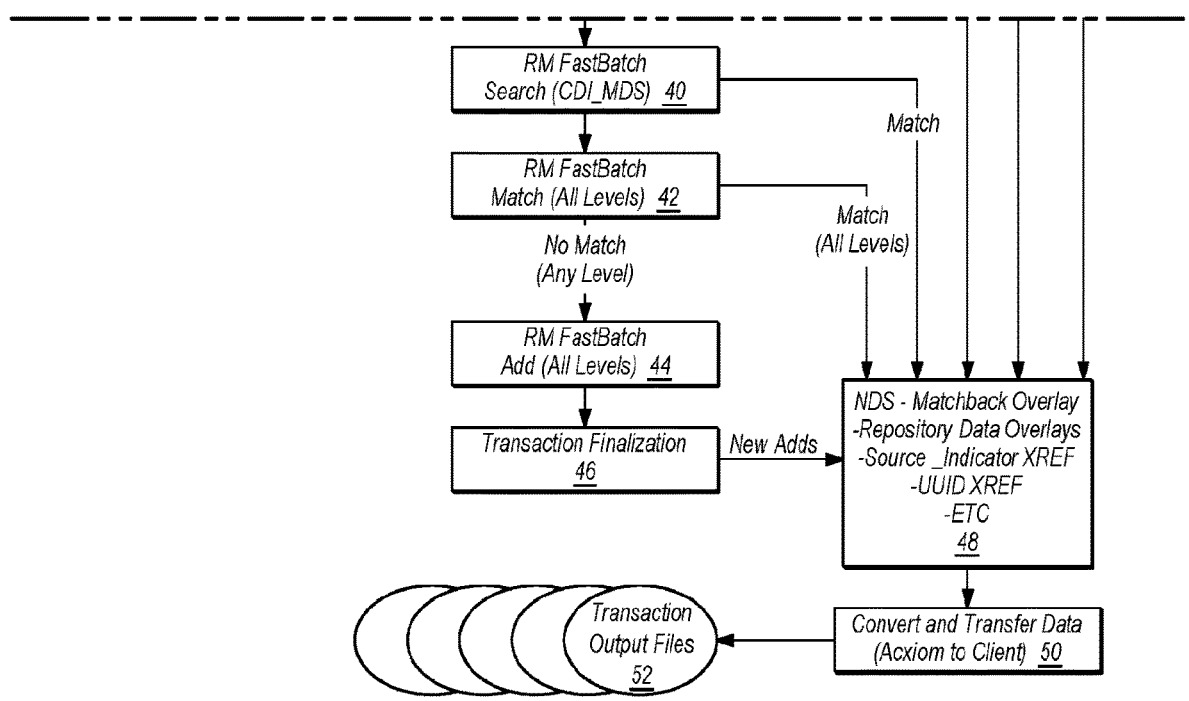

Using the same recognition system as in the test just described, a further test was performed to validate the overall accuracy of the system and method. An $n^{th}$ (random) sample test bed was created and manually audited from the business record set. In order to prevent bias, this sample test bed of 1,022 total groups encompassed all group size categories and reflected all FGQG ranges (grades range from 1-100). It was observed that an FGQG of 60 or higher was found for 511 groups out of the 1,022 groups sampled. In other words, 50% of the total groups sampled received an FGQG of 60 (i.e., 60%) or higher. In addition, 16.6% of the total groups sampled received an FGQG of 90% or higher. FIG. 2-A illustrates the overall business accuracy as a pie chart and FIG. 2-B breaks down the business accuracy results by FGQG size ranges.

Again using the same marketing technology platform with the same marketing database, the implementation of the invention as described herein was applied to the bi-monthly refresh process data file. This process takes the oldest repository identifiers (total records include $\frac{1}{13}^{th}$ of the full data repository base) and re-processes them through data recognition to apply any necessary changes caused from internal product enhancements. Next, all records are then assigned a new link, and new repository identifiers are assigned where necessary. In turn, this process ensures consistency across the database and data repository to formulate a single and accurate view of the customer. The bi-monthly refresh data file selected for testing consisted of 148,396,077 records, and it processed for approximately 249.6 hours. After applying the implementation of the invention as described herein, the size of the bi-weekly refresh data was reduced by 10,899,000 records (a reduction in record size by more than 7%), and total processing time was reduced by 19.2 hours. The dramatic improvement thus achieved is graphically represented by the pie charts of FIGS. 3-A and 3-B. The monthly refresh data file selected for testing consisted of 296,792,154 records, and it processed for approximately 499.2 hours. After applying the implementation of the invention as described herein, the size of the monthly refresh data was reduced by 21,798,000 records, and total processing time was reduced by 38.5 hours, representing a processing time improvement of more than 7%. The dramatic improvement thus achieved on a monthly basis is graphically represented by the pie charts of FIGS. 3-C and 3-D.

Again using the same marketing technology platform with the same marketing database, the implementation of the invention as described herein was applied to another test environment. This test environment consisted of 626,260,073 records and at rest the data consumed a total space of 550 GB. Processing this set of records before applying this system and method required an allocation of 3.1 TB. The following three test cases utilized the environment as defined above.

Figure 5A:
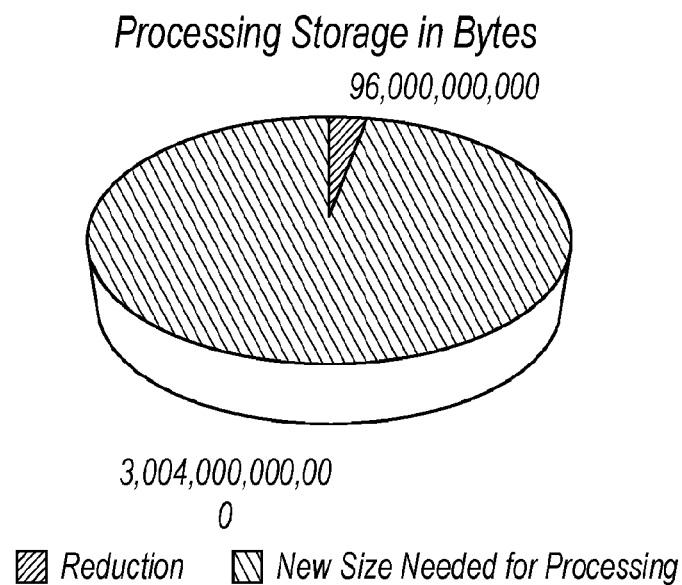
FIG. 5-A is an overview of the reductions in hard disc storage requirements for processing observed when implementing an embodiment of the invention on a identity resolution data repository.
Figure 5B:
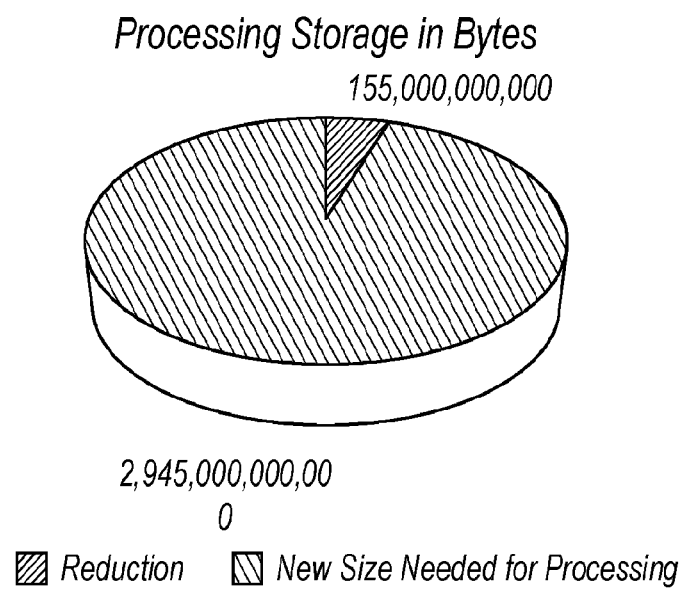
Figure 5C:
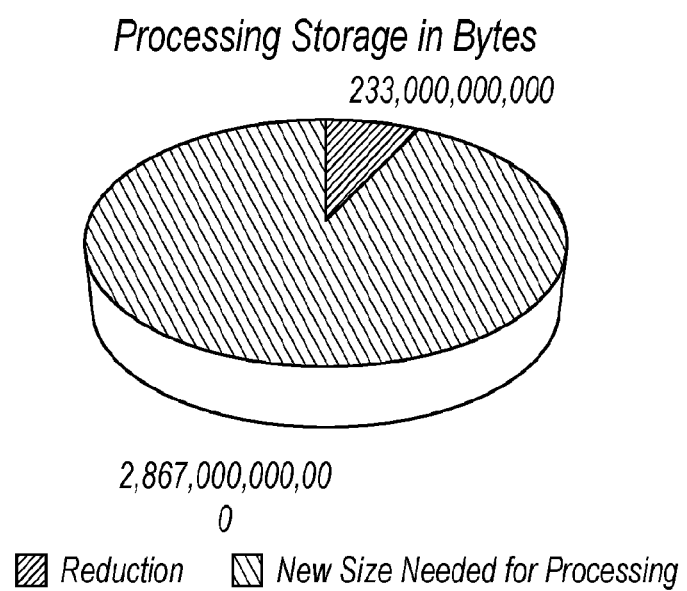

Test case 1 utilized a very conservative, in regard to data recall, threshold score of 30 and reduced the number of records sent in for processing by 17,264,573 records or 2.8%. This reduction of records equates to a storage savings of 17 GB or 3%. This reduction also minimizes the allocated space for processing. With the set threshold score of 30 the requirements were reduced by 96 GB or 3%. The improvement in storage requirements is graphically represented by the pie chart of FIG. 5-A.

Test Case 2 utilized a slightly less conservative, in regard to data recall, threshold score of 40 and reduced the number of records sent in for processing by 29,883,069 records or 4.8%. This reduction of records equates to a storage savings of 27.5 GB or 5%. This reduction also minimizes the allocated space for processing. With the set threshold score of 40 the requirements were reduced by 155 GB or 5%. The improvement in storage requirements is graphically represented by the pie chart of FIG. 5-B.

Test Case 3 utilized an even less conservative, in regard to data recall, threshold score of 50 and reduced the number of records sent in for processing by 47,053,346 records or 7.5%. This reduction of records equates to a storage savings of 41.5 GB or 5%. This reduction also minimizes the allocated space for processing. With the set threshold score of 50, the requirements were reduced by 233 GB or 7.5%. The improvement in storage requirements is graphically represented by the pie chart of FIG. 5-C.

Test Cases 1-3 were used to demonstrate the data transfer times and network resource allocations created by implementing the system and method. These savings can be measured downstream during data transfer using ftp, sftp, or an sftp connection utilizing connect direct. Assuming a transfer speed of 30 Mbps and an original file size of 550 GB, the transfer time would be around 1 Day, 19 Hours, and 45 Minutes. This system and method can bring that transfer time down to anywhere between 1 Day, 16 Hours, and 27 minutes (an improvement of over 6%) to 1 Day, 18 Hours, and 24 Minutes. This can also reduce the bandwidth allocation required if these resources were required for another network transaction and still yield the same transfer time as the original file. Assuming an original file size of 550 GB and a transfer time around 1 Day, 19 Hours, and 45 Minutes a transfer speed of 30 Mbps would be required. With the system and method put in place the file size would be down to anywhere between 508.5 GB to 533 GB, which would only require transfer speeds of 28 Mbps to 29 Mbps to complete the transfer in a similar time.

It may thus be understood that the implementation of the invention described above provides users of a database containing data structures pertaining to objects, such as a marketing database containing records, to determine the overall group quality for solutions utilizing data recognition in that database. This allows users to suppress groups deemed to be of low quality based off of a desired threshold cutoff value, which may be modified based on the desired risk level and the particular application. Because this approach is objective and its parameters are easily modified, it allows business rule logic to be changed to meet new and ever-changing industry demand. It further allows for faster processing and a smaller database footprint, thus leading to significant cost savings related to the technology used to implement this implementation of the invention.

Figure 4B:
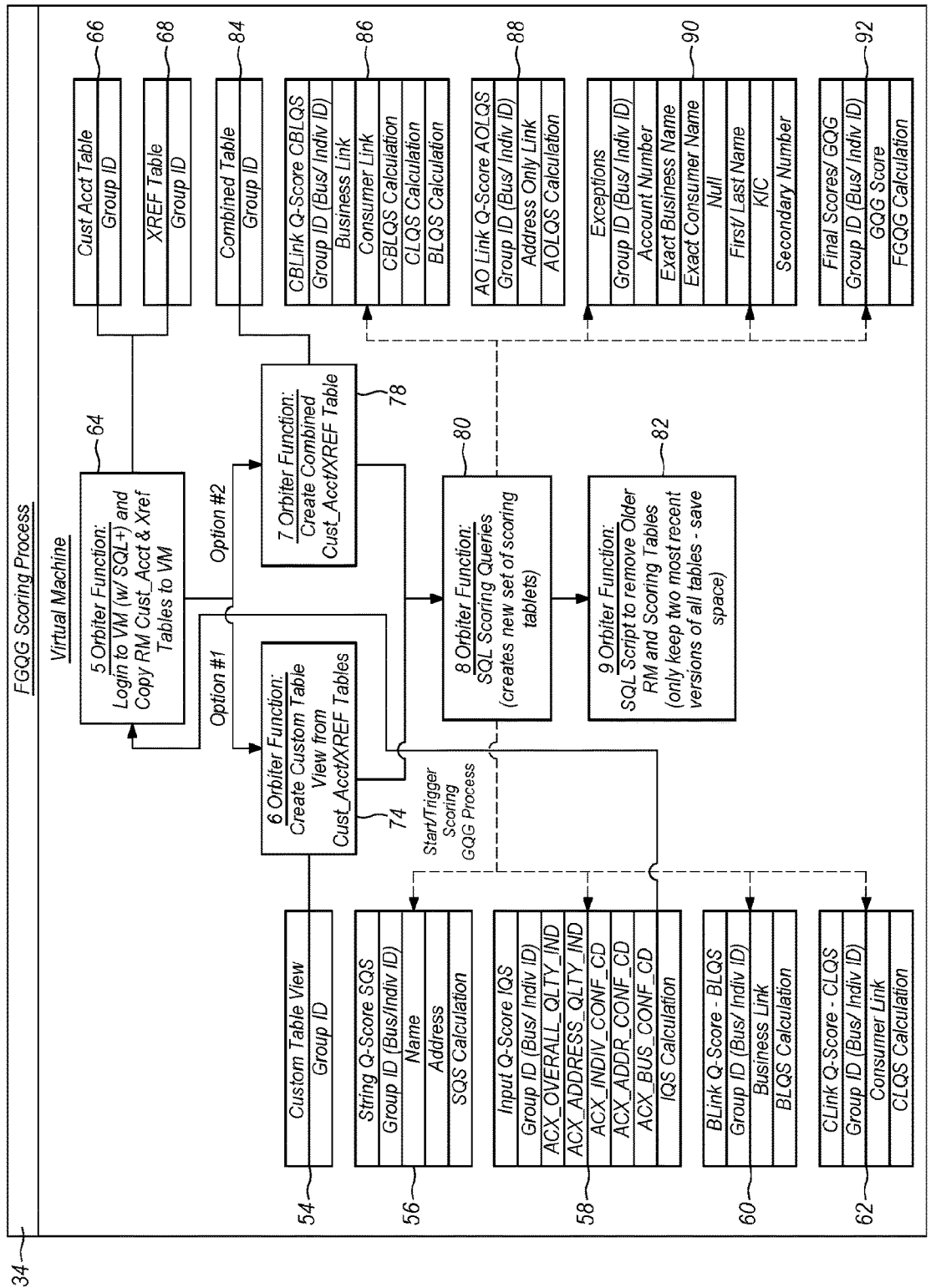
FIG. 4-A is a high-level overview of a data recognition process according to an embodiment of the invention.

The invention as described herein is intended for use as part of an overall recognition system, one example of which is illustrated by FIG. 4-A. Input file 10 may represent, for example, a data file from a merchant that contains consumer or business records. These files are transferred to the marketing services provider at block 12. A first search is done of the data based on customer account identifier (Cust_Acct_ID), and matches are identified and sent to match overlay block 48. At block 16 source data manipulations are performed in order to standardize the remaining data for further processing. At step 18, the data is then split according to the type of data each record represents: in this example, the data is split into global data group 20, US data group 22, partial data group 24, and other (i.e., rejected data that could not be otherwise classified) into group 26. The data from group 26 proceeds immediately to overlay block 48, while the other data undergoes further processing.

Partial data group 24 is ingested at data append services 32, with the purpose being to append data to make the data from partial data group 24 whole and thus usable. This may include, for example, determining a best address for a data record. Rejects (i.e., no match can still be found) are sent then directly to overlay block 48. Matches are sent to US hygiene/data quality block 30, which is also the place where US data group 22 is sent. At US hygiene/data quality block 30, the data is standardized, cleansed, and updated. This may include, for example, identifying name anomalies, such as abbreviations, misspellings, formatting issues, incomplete content, and other miscellaneous content issues. It can include improvements to address information, such as corrections to verify delivery points, occupancy-based improvements, new movers, and other miscellaneous content issues. It may include evaluating email addresses, syntax validations/corrections, and email change of address (COA). It may also include telephone confirmation or corrections, NPA/NXX content validations, realignment of area codes, identification of land-line versus mobile, and the ability to flag private phones and suppressions. A similar process is performed for global data group 20 at global hygiene/data quality block 28.

The FGQG scoring block 34 is performed after data moves from US hygiene/data quality block 30. In this example FGQG scoring is performed only on US data, but the invention is not so limited. This block will be described in detail with reference to FIG. 4-B below. An additional re-hygiene/data quality process is performed at block 36, and the output of block 36 joins with the output of block 28 as an input to final data quality manipulations block 38. Processing then moves to search based on customer link block 40, where if a match occurs the data is moved to overlay block 48. If no match is found, then at matching block 42 matching is performed on all levels, not just customer link, and again if a match is found then the data is moved to overlay block 48. Remaining data for which no match is found is sent to block 44 to be added to the database, after which a transactional finalization is performed at block 46 for new records to be added, and this final thread of the processing moves to overlay block 48.

At overlay block 48, the new data that has been received by the marketing services provider and that has now been processed through the recognition system is overlaid onto the main repository database. Transaction output files 52 are then converted and transferred back to the marketer at block 50.

Turning now to FIG. 4-B, the processing within FGQG scoring block 34 may be described in more detail. This processing is illustrated as a "virtual machine" consisting of processes and data inputs and outputs, although it may be implemented on either specially purposed computing hardware or specially programmed general-purpose computing hardware. Processing begins at subroutine 64, where the user may log in to the virtual machine (VM) and copy the recognition manager (RM) customer account identifier (Cust_Acct) and cross-reference tables to the virtual machine. Inputs here are the customer account table 66 and the cross-reference table 68. Processing proceeds to either option #1, block 70, for a custom table view, or option #2, block 72, for the creation of a combined customer account/cross-reference table. These processes are performed at blocks 74 and 78, respectively. Outputs from block 74 are custom table view 54 and outputs from block 78 are combined table 84. Block 76 starts the FGQG scoring process, which is performed by a series of scoring queries in SQL at block 80. The outputs here match the various scores that are described in the calculations provided above, and include string quality score SQS at block 56, input quality score IQS at block 58, business link quality score BLQS at block 60, customer link quality score CLQS at block 62, customer/business link quality score CBLQS at block 86, address-only quality link score AOLQS at block 88, exceptions at block 90, and final group quality grade score FGQG at block 92. Finally, at block 92 clean-up operations are performed, as older recognition management and sorting tables are removed, since only the most recent versions are retained of all tables in order to conserve storage space.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. When a grouping is used herein, all individual members of the group and all combinations and sub combinations possible of the group are intended to be individually included. When a range is stated herein, the range is intended to include all subranges and individual points within the range. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention, as set forth in the appended claims.

The invention claimed is:

1. A method for improving recognition quality and thereby improve computing performance for a database comprising a plurality of data structures each pertaining to one of a plurality of objects, comprising the steps of:
   a. concatenating a plurality of fields containing strings in each of a plurality of data structures pertaining to one of the objects, and calculating a string quality score (SGS) based on the similarity of the concatenated strings;
   b. calculating an input quality score (IQS) for the object based on a weighted measure of a plurality of input overall quality scores and input confidence scores;
   c. calculating a link quality score (LQS) for the object, with inputs to the LQS calculating comprising the number of unique links, a number of data structures associated with the object, a count of the unique link that occurs most often, and a ratio of the number of unique links to the number of data structures;
   d. applying a plurality of LQS exceptions to the LQS score for the object to determine if any of the LQS exceptions apply and thereby override the previously calculated LQS for the object by replacing the previously calculated LQS for the object with a pre-defined LQS value associated with such LQS exception;
   e. calculating a group quality grade (GQG) for the object based on a weighted measure of the SGS, IQS, and LQS, wherein the GQG is a single numerical value falling within a defined range;
   f. applying a plurality of GQG exceptions to the GQG score for the object to determine if any of the GQG exceptions apply and override the previously calculated GQG for the object by replacing the previously calculated GQG for the object with a pre-defined GQG value associated with such GQG exception to produce a final GQG (FGQG); and
   g. repeating the foregoing steps for a plurality of objects in the database, and applying a cut-off threshold FGQG value to the database such that objects below the cut-off threshold FGQG value are suppressed in the database, wherein the plurality of objects in the database after suppression comprises a smaller number of objects than prior to application of the method steps hereof.

2. The method of claim 1, wherein the step of calculating a GQG for the object further comprises the step of determining a group size for the object, wherein the group size is a measure of the number of separate data structures grouped in the object.

3. The method of claim 2, wherein the step of calculating an LQS for the object comprises the steps of calculating (a) either a customer business link quality score (CBLQS) or a customer link quality score (CLQS) and (b) an address only link quality score (AOLQS) for the object.

4. The method of claim 3, wherein the object is classified as being one of a plurality of group sizes based on the number of data structures pertaining to the object, and wherein the weights applied to calculate the GQG value are determined based on the group size of the object.

5. The method of claim 4, wherein the plurality of group sizes consists of three group sizes, and wherein at least one of the weights applied to calculate the GQG value for each of the three group sizes are different.

6. The method of claim 3, wherein the object comprises a plurality of data structures pertaining to a business group, and the step of calculating either a CBLQS or a CLQS consists of the step of calculating a CBLQS.

7. The method of claim 6, wherein the object comprises 20 or fewer data structures, and the weights applied in calculating the GQG value are 0.10 for the SQS value, 0.40 for the IQS value, 0.30 for the CGLQS value, and 0.20 for the AOLQS value.

8. The method of claim 6, wherein the object comprises 21-50 data structures, and the weights applied the GQG value are 0.10 for the SQS value, 0.25 for the IQS value, 0.40 for the CBLQS value, and 0.25 for the AOLQS value.

9. The method of claim 6, wherein the object comprises more than 50 data structures, and the weights applied the GQG value are 0.10 for the SQS value, 0.00 for the IQS value, 0.30 for the CBLQS value, and 0.20 for the AOLQS value.

10. The method of claim 3, wherein the object comprises a plurality of data structures pertaining to a consumer group, and the step of calculating either a CBLQS or a CLQS comprises the step of calculating a CLQS.

11. The method of claim 10, wherein the object comprises 20 or fewer data structures, and the weights applied in calculating the GQG value are 0.10 for the SQS value, 0.40 for the IQS value, 0.30 for the CLQS value, and 0.20 for the AOLQS value.

12. The method of claim 10, wherein the object comprises 21-50 data structures, and the weights applied the GQG value are 0.10 for the SQS value, 0.40 for the IQS value, 0.30 for the CLQS value, and 0.20 for the AOLQS value.

13. The method of claim 10, wherein the object comprises more than 50 data structures, and the weights applied the GQG value are 0.10 for the SQS value, 0.40 for the IQS value, 0.30 for the CLQS value, and 0.20 for the AOLQS value.

14. A system for improving recognition quality by reducing a total number of a plurality of objects in a database, comprising:
   a. a plurality of data structures stored on the database, each of the plurality of data structures pertaining to one of the plurality of objects;
   b. a recognition quality routine implemented on specially programmed general-purpose computing hardware, wherein the recognition quality routine comprises:
      i. a string quality score (SGS) subroutine implemented on the specially programmed general-purpose computing hardware and configured to concatenate a plurality of fields containing strings in each of a plurality of data structures pertaining to the object, and calculating an SGS based on the similarity of the concatenated strings;
      ii. an input quality score (IQS) subroutine implemented on the specially programmed general-purpose computing hardware and configured to calculate an IQS for the object based on a weighted measure of a plurality of input overall quality scores and input confidence scores; and
      iii. a link quality score (LQS) subroutine implemented on the specially programmed general-purpose computing hardware and configured to:
         calculate an LQS for the object by counting a number of unique links, a number of data structures associated with the object, a count of the unique link that occurs most often, and a ratio of the number of unique links to the number of data structures; and
         2. determine if any of a plurality of LQS exceptions apply and thereby override the previously calculated LQS for the object by replacing the previously calculated LQS for the object with a pre-defined LQS value associated with such LQS exception;
      iv. a group quality grade (GQG) subroutine implemented on the specially programmed general-purpose computing hardware and configured to:
         1. calculate a GQG for the object based on a weighted measure of the SGS, IQS, and LQS, wherein the GQG is a single numerical value falling within a defined range; and
         2. applying a plurality of GQG exceptions to the GQG score for the object to determine if any of the GQG exceptions apply and override the previously calculated GQG for the object by replacing the previously calculated GQG for the object with a pre-defined GQG value associated with such GQG exception to produce a final GQG (FGQG); and
      v. a cut-off threshold routine implemented on the specially programmed general-purpose computing hardware and configured to apply a cut-off threshold FGQG value to the database such that objects with an FGQG below the cut-off threshold FGQG value are suppressed in the database, wherein the total number of objects in the database after application of the cut-off threshold routine is less than the total number of objects in the database prior to application of the cut-off threshold routine.

15. The system of claim 14, wherein the recognition quality routine is further configured to determine a group size for the object, wherein the group size is a measure of the number of separate data structures grouped in the object.

16. The system of claim 15, wherein the LQS subroutine is further configured to calculate (a) either a customer business link quality score (CBLQS) or a customer link quality score (CLQS) and (b) an address only link quality score (AOLQS) for the object.

17. The system of claim 16, wherein the recognition quality routine is further configured to assign the object to one of a plurality of group sizes based on the number of data structures contained in the object, and wherein the GQG subroutine is further configured to determine the GQG value based on the group size of the object.

18. The system of claim 17, wherein the plurality of group sizes consists of three group sizes, and wherein at least one of the weights applied to calculate the GQG value for each of the three group sizes are different.

19. The system of claim 16, wherein the object comprises a plurality of data structures pertaining to a business group, and wherein the LQS subroutine is further configured to calculate a CBLQS.

20. The system of claim 19, wherein the object comprises 20 or fewer data structures, and wherein the GQG subroutine is configured to apply, in calculating the GQG value, the weights of 0.10 for the SQS value, 0.40 for the IQS value, 0.30 for the CGLQS value, and 0.20 for the AOLQS value.

21. The system of claim 19, wherein the object comprises 21-50 data structures, and wherein the GQG subroutine is configured to apply, in calculating the GQG value, the weights of 0.10 for the SQS value, 0.25 for the IQS value, 0.40 for the CBLQS value, and 0.25 for the AOLQS value.

22. The system of claim 19, wherein the object comprises more than 50 data structures, and wherein the GQG subroutine is configured to apply, in calculating the GQG value, the weights of 0.10 for the SQS value, 0.00 for the IQS value, 0.30 for the CBLQS value, and 0.20 for the AOLQS value.

23. The system of claim 16, wherein the object comprises a plurality of data structures pertaining to a consumer group, and wherein the LQS subroutine is further configured to calculate a CLQS.

24. The system of claim 23, wherein the object comprises 20 or fewer data structures, and wherein the GQG subroutine is configured to apply, in calculating the GQG value, the weights of 0.10 for the SQS value, 0.40 for the IQS value, 0.30 for the CLQS value, and 0.20 for the AOLQS value.

25. The system of claim 23, wherein the object comprises 21-50 data structures, and wherein the GQG subroutine is configured to apply, in calculating the GQG value, the weights of 0.10 for the SQS value, 0.40 for the IQS value, 0.30 for the CLQS value, and 0.20 for the AOLQS value.

26. The system of claim 23, wherein the object comprises more than 50 data structures, and wherein the GQG subroutine is configured to apply, in calculating the GQG value, the weights of 0.10 for the SQS value, 0.40 for the IQS value, 0.30 for the CLQS value, and 0.20 for the AOLQS value.

27. A method for improving recognition quality, comprising the steps of:

a. concatenating a plurality of fields containing strings in each of a plurality of data structures in a database each pertaining to one of a plurality of objects, and calculating a string quality score (SGS) based on the similarity of the concatenated strings;

b. calculating an input quality score (IQS) for the object based on a weighted measure of a plurality of input overall quality scores and input confidence scores;

c. calculating a link quality score (LQS) for the object, with inputs to the LQS calculating comprising the number of unique links, a number of data structures associated with the object, a count of the unique link that occurs most often, and a ratio of the number of unique links to the number of data structures;

d. calculating a group quality grade (GQG) for the object based on a weighted measure of the SGS, IQS, and LQS, wherein the GQG is a single numerical value falling within a defined range; and e. repeating the foregoing steps for a plurality of objects in the database, and applying a cut-off threshold final group quality grade (FGQG) value to the database such that objects below the cut-off threshold FGQG value are suppressed in the database, wherein the plurality of objects in the database after the step of the application of the cut-off threshold FGQG value comprises at least three percent (3%) fewer objects than prior to application of the method steps hereof.

28. The method of claim 27, further comprising the step of applying a refresh to the database after the step of the application of the cut-off threshold FGQG value, and wherein the refresh step is performed at least 7% more quickly than would be performed prior to the application of the method steps hereof.

29. The method of claim 27, wherein the database occupies a storage space that is at least 3% smaller after the application of the cut-off threshold FGQG value step.

\* \* \* \* \*